United States Patent [19]

Smith

[11] Patent Number: 5,414,107

[45] Date of Patent: May 9, 1995

[54] PROCESS FOR RECYCLING POLYETHYLENE TEREPHTHALATE PROCESS RESIDUES CONTAINING ALKALI METAL ORGANIC SALTS

[75] Inventor: Brad L. Smith, Wilmington, N.C.

[73] Assignee: Hoechst Celanese Corporation, Somerville, N.J.

[21] Appl. No.: 277,685

[22] Filed: Jul. 20, 1994

[51] Int. Cl.⁶ .............................................. C07C 67/48
[52] U.S. Cl. ...................................... 560/79; 560/78; 560/96
[58] Field of Search .............................. 560/78, 79, 96

[56] References Cited

U.S. PATENT DOCUMENTS

| 2,884,443 | 4/1959 | Siggel et al. | 260/475 |
|---|---|---|---|
| 3,037,050 | 5/1962 | Heisenberg et al. | 260/475 |
| 3,148,208 | 9/1964 | Siggel et al. | 260/475 |
| 3,321,510 | 5/1967 | Lotz et al. | |
| 3,488,298 | 1/1970 | Barkey et al. | 260/2.3 |
| 3,907,868 | 9/1975 | Currier et al. | 260/475 |
| 4,078,143 | 3/1978 | Malik et al. | 560/78 |
| 4,118,582 | 10/1978 | Walker | 560/96 |
| 4,154,921 | 5/1979 | Singh | 528/275 |
| 4,163,860 | 8/1979 | Delattre et al. | 560/96 |
| 4,542,239 | 9/1985 | Lamparter et al. | 562/487 |
| 4,578,502 | 3/1986 | Cudmore | 560/79 |
| 5,051,528 | 9/1991 | Naujokas et al. | 560/78 |

OTHER PUBLICATIONS

Encyclopedia of Chemical Technology vol. 18, Third Edition, John Wiley & Sons, New York, NY (1982) pp. 534–536.

*Primary Examiner*—José G. Dees
*Assistant Examiner*—Samuel Barts
*Attorney, Agent, or Firm*—R. H. Hammer, III

[57] ABSTRACT

A process for recycling by-products produced from a process for the manufacture of polyethylene terephthalate is disclosed. The process includes the steps of: (a) providing ethylene glycol distillation bottoms from an ethylene glycol recovery unit associated with the manufacture of polyethylene terephthalate, the bottoms containing an alkali metal organic salt produced during the manufacture of polyethylene terephthalate, the alkali metal organic salt being in excess of about 100 ppm of the bottoms; (b) stripping the alkali metal from the organic acid by use of a strong acid; and (c) depolymerizing the organic acid.

7 Claims, 1 Drawing Sheet

PROCESS FOR RECYCLING POLYETHYLENE TEREPHTHALATE PROCESS RESIDUES CONTAINING ALKALI METAL ORGANIC SALTS

FIELD OF THE INVENTION

This invention is directed toward a process for recycling by-products produced from a process for manufacture of polyethylene terephthalate (PET). These by-products, e.g., ethylene glycol distillation bottoms, contain alkali metal organic salts.

BACKGROUND OF THE INVENTION

Polyethylene terephthalate (PET) is a polyester polymer that is produced commercially, e.g., in a two step polymerization process. See: Kirk-Othmer, *Encyclopedia of Chemical Technology,* Third Edition, Vol.18, John Wiley & Sons, New York, N.Y. (1982) p. 534–536. This process generally comprises an esterification step and a polycondensation step. The esterification step may be either: a monomer formation by an ester interchange of dimethyl terephthalate (DMT) with ethylene glycol; or esterification of terephthalic acid (TA) with ethylene glycol. In either case, a monomer called bis-(2-hydroxyethyl) terephthalate (BHET) is formed.

During the polycondensation step, the monomer (BHET) is heated which causes the monomer to condense with itself to form polyethylene terephthalate. As the monomer condenses, ethylene glycol is liberated and removed, e.g. under vacuum. The material removed by vacuum ("overhead") contains ethylene glycol as well as some dimethyl terephthalate (DMT), monomer, and polycondensation catalyst. Typically, this overhead is stripped of excess ethylene glycol leaving a bottoms stream containing some residual ethylene glycol, monomer, and oligomer as well as the catalyst (e.g., 0.2 to 1% antimony, manganese, titanium, phosphorus).

Processes for the recycling of PET waste streams are known. "Methanolysis" is one such process. In methanolysis, the PET material is reacted with methanol to produce dimethyl terephthalate (DMT). For example, see U.S. Pat. Nos. 2,884,443; 3,037,050; 3,148,208; 3,321,510; 3,488,298; 3,907,868; 4,163,860; 4,578,502; and 5,051,528. "Glycolysis" is another process for recycling PET production waste. In "glycolysis", PET scrap is reacted with ethylene glycol to produce bis-(2-hydroxyethyl) terephthalate (BHET), the PET monomer. For example, see U.S. Pat. No. 4,078,143, column 1.

In the effort to recover excess ethylene glycol from the overhead of the polycondensation process, alkali metal compounds may be added to saponify the residual DMT and thereby improve the ethylene glycol recovery efficiency. It may be added for other reasons, which are incorporated herein by reference, see U.S. Pat. Nos. 4,118,582; 4,154,921. The addition of alkali metal compounds results in the formation of alkali metal salts of terephthalic acid, hydroxyethylterephthalate, or higher oligomer having an organic acid functional group. These salts lower the efficacy of the known recycling processes because they are inert in these processes.

Accordingly, there is a need for a process to convert these organic salts to a form that will react in recycle processes, and thereof increase the efficacy of those processes.

SUMMARY OF THE INVENTION

A process for recycling by-products produced from a process for the manufacture of polyethylene terephthalate is disclosed. The process includes the steps of: (a) providing ethylene glycol distillation bottoms from an ethylene glycol recovery unit associated with the manufacture of polyethylene terephthalate, the bottoms containing an alkali metal organic salt produced during the manufacture of polyethylene terephthalate, the alkali metal organic salt being in excess of about 100 ppm of the bottoms; (b) stripping the alkali metal from the organic acids by use of a strong acid; and (c) depolymerizing the organic acid.

DESCRIPTION OF THE DRAWING

For the purpose of illustrating the invention, there is shown in the drawing a form which is presently preferred; it being understood, however, that this invention is not limited to the precise arrangements and instrumentalities shown.

DESCRIPTION OF THE INVENTION

Figure 1:
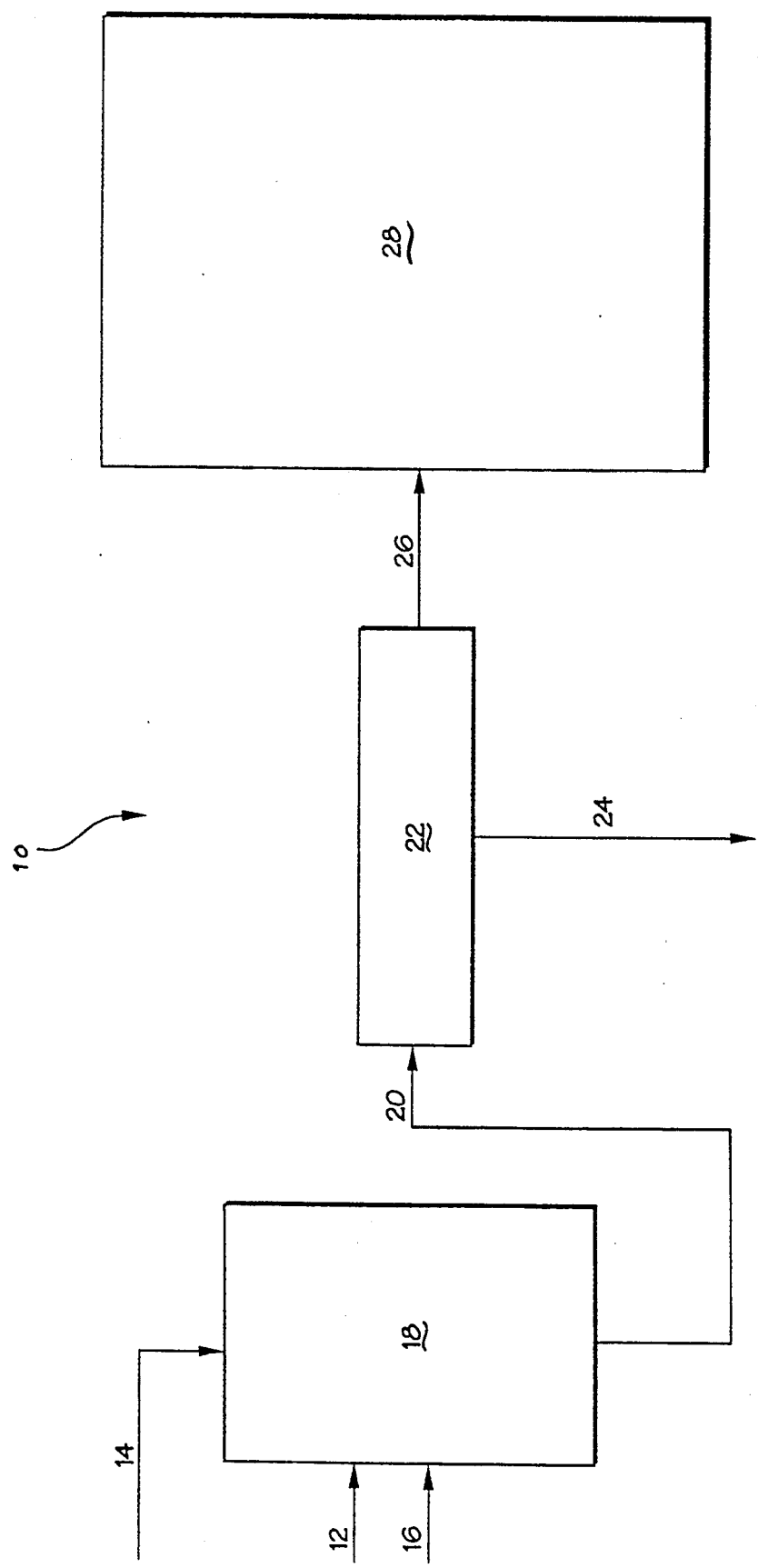
FIG. 1 is a schematic of the present invention.

Referring to FIG. 1, there is shown a process 10 for recycling by-products produced from a process for the manufacture of polyethylene terephthalate (PET).

In process 10, the by-product 12, and preferably water 14, is charged into mixing vessel 18. If water is used, the weight ratio of by-product to water is about 1:1. The by-product 12 is preferably the ethylene glycol distillation bottoms (discussed in detail below) from the manufacture of polyethylene terephthalate and contains at least about 100 ppm of an alkali metal organic salt (discussed in detail below). The by-product/water mixture is acidified with a strong acid 16 (discussed in detail below), so that it achieves a pH of <2. As a result of acidification, the alkali metals are stripped from the organic acids. After stripping, a mixture 20 of water, inorganic salts, and organic acids are formed. Preferably, the acidified mixture 20 of by-product/water is passed to dewatering means 22 that separates the water/inorganic salts 24 from the organic acids 26. The stream of water/inorganic salts 24 is disposed of in any conventional manner. The stream 26 containing the organic acids is passed to vessel 28 where it is depolymerized (discussed in detail below).

As discussed above, the process for the manufacture of polyethylene terephthalate is well known. See, Kirk-Othmer, *Encyclopedia of Chemical Technology,* Third Edition, volume 18, John Wiley & Sons, New York, N.Y., (1982), p. 534–536, which is incorporated herein by reference. The process generally comprises an esterification step and a polycondensation step. During the esterification step, terephthalic acid (TA) or dimethyl terephthalate (DMT) is reacted with ethylene glycol (also known as "glycol") to form bis-(2-hydroxyethyl) terephthalate (BHET). During the polycondensation step, the BHET is condensed, i.e., excess ethylene glycol is removed, to form polyethylene terephthalate. The source material for the inventive process is preferably, but not necessarily, from the manufacture of polyethyelene terephthalate. Any source material rich in PET, BHET, or DMT and containing the alkali metal organic salts could be treated in the inventive process.

As with any chemical process, by-products other than BHET or PET are formed. "By-products", as used herein, refers to, among other things, any non-PET or non-BHET material formed in the manufacture of PET. More specifically, it includes the oligomers (e.g. dimers, trimers, and tetramers of DMT or TA and ethylene glycol), and cyclic oligomers. These by-products also include alkali metal organic salts. The by-products may be collected from the process for manufacturing PET at the ethylene glycol recovery unit, as ethylene glycol distillation bottoms.

"Ethylene glycol distillation bottoms", as used herein, refers to the non-ethylene glycol portion taken from the bottom of the distillation column in the ethylene glycol recovery unit associated with the process for the manufacture of PET. This waste generally comprises bis-(2-hydroxyethyl) terephthalate (BHET), oligomers, ethylene glycol, alkali metal organic salts, and catalysts.

"Alkali metal organic salt", as used herein, refers to a salt comprising an alkali metal and an organic acid. The alkali metal is any element from Group IA of the periodic table (i.e., lithium, sodium, potassium, rubidium, cesium, and francium). Most likely, however, the alkali metal is sodium. As discussed above, the alkali metals may come from compounds added to the wastes stream to improve, among other things, the removal efficiencies of ethylene glycol. The organic acid could be any monomer having an organic acid functional group that is produced in the PET manufacturing process. These alkali metal organic salts may exist in the ethylene glycol distillation bottoms in excess of 100 ppm to 10,000 ppm or more. If the ethylene glycol distillation bottoms contain more than 100 ppm alkali metal organic salts, this process can effectively reduce the amount of those salts.

"Stripping", as used herein, refers to the removal of the alkali metal from the organic acid of the alkali metal organic salt. Preferably, stripping is accomplished by acidifying the ethylene glycol distillation bottoms with a strong acid. A sufficient amount of strong acid should be used, so that the pH of the mixture containing alkali metal organic salt is less than or equal to 2. Preferably, prior to acidifying the ethylene glycol distillation bottoms, it is mixed with water to facilitate mixing. Preferably, the weight ratio of ethylene glycol distillation bottoms to water is about 1:1. The acidification may be conducted in any conventional fashion, e.g. in a batch-wise or a continuous manner. In a batch-wise process, the acidification is conducted in a conventional mixing vessel. Optionally, after stripping, the acidified stream 20 may be neutralized in any known manner.

"Strong acid", as used herein, refers to a protonic acid which when added to $H_2O$ results in solutions of $pH \leq 2$. The strong acids include, but are not limited to: sulfuric acid ($H_2SO_4$), hydrochloric acid (HCl), nitric acid ($H_2NO_3$), phosphoric acid ($H_2PO_4$) and combinations thereof. Preferably, the acid is hydrochloric acid (HCl).

"Dewatering", as used herein, refers to a method of removing water and any entrained inorganic salts from the stream 20 exiting the mixing vessel 18. Dewatering may be accomplished by filtration or centrifugation, both well known in the art. The amount of water removed depends upon the subsequent depolymerization step. For example, if methanolysis is the first or only depolymerization step, the material should be dewatered to about 1% by weight, but if glycolysis is used, more water can be tolerated.

"Depolymerizing", as used herein, refers to either: degradation of the organic acid into a monomeric material suitable for recondensation into PET; or complete decomposition to DMT. Depolymerization processes include "glycolysis", "methanolysis", or a combination of both these methods. Explemary methanolysis processes include U.S. Pat. Nos. 2,884,443; 3,037,050; 3,148,208; 3,321,510; 3,488,298; 3,907,868; 4,163,860; 4,578,502; and 5,051,528, each of which is incorporated herein by reference. An explemary glycolysis is disclosed in U.S. Pat. No. 4,078,143, column 1, which is incorporated herein by reference. Preferably, depolymerization includes glycolysis followed by methanolysis.

The invention will now be described in greater detail by way of the following non-limiting examples.

EXAMPLE 1

Example 1 demonstrates that the alkali metal can be removed from an organic acid using the process of FIG. 1.

Ethylene glycol distillation bottoms containing about 9000 ppm of sodium organic salt was prestripped of excess ethylene glycol. The bottoms (87 grams) were heated until liquified. Water (100 grams) at room temperature was added to the liquified bottoms while stirring. Concentrated sulfuric acid was added until the pH was less than 2 at which point the mixture was dewatered by filtration. Sodium analysis of the bottoms showed only 6 ppm sodium remained.

EXAMPLE 2

Example 2 demonstrates that alkali metal salts of terephthalic acid (TA) or the mono-methyl ester of TA are not readily converted to dimethyl terephthalate (DMT) under methanolysis conditions.

29.3 grams of the potassium salts of mono-methyl terephthalate, 130.8 grams of methanol, and 0.40 grams of manganese acetate (esterification catalyst) were charged into a pressure vessel, sealed, and heated at 170° C. for two hours. Afterwards, the contents were removed and analyzed by gas chromatography. A gas chromatography analysis showed only 7% of the theoretical yield of DMT was obtained.

EXAMPLE 3

Example 3 demonstrates that alkali metal salts of terephthalic acid (TA) or the mono-methyl ester of TA are not readily converted to bis-(2-hydroxyethyl) terephthalate (BHET) by glycolysis. This example also illustrates that if the alkali metal salts are stripped with strong acid to form an organic acid and then subjected to glycolysis, then BHET will result.

Two glass vessels were placed side-by-side and each charged with 100 grams of the potassium salt of monomethyl terephthalate and 500 grams of ethylene glycol. To one of the reactors, 50 mL of 37% hydrochloric acid (HCl) was added to strip the potassium from the monomethyl terephthalate. Both reactors were heated to the reflux temperature (>200° C.) and the overhead product was removed periodically to maintain an overhead temperature of greater than 190° C. (The overhead temperature dropped as water was released). Samples were taken periodically and analyzed by gas chromatography. After four hours of refluxing, the solutions were cooled. The gas chromatography analysis showed that the sample in which HCl was added was converted to bis-(2-hydroxyethyl) terephthalate (BHET) with a yield of 87% of theoretical. In contrast, the sample which was not stripped resulted in a yield of 22% of theoretical.

The stripped material which was mostly BHET was placed into a methanolysis vessel along with four weight equivalents of methanol and 1000 ppm Mn (added as manganese acetate) and heated at 170° C. for two hours. The contents were then removed and analyzed by gas chromatography and resulted in a DMT yield of 97% of theoretical maximum. The present invention may be embodied in other specific forms without departing from the spirit or essential attributes thereof and, accordingly, reference should be made to the appended claims, rather than to the foregoing specification, as indicating the scope of the invention.

I claim:

1. A process for recycling by-products produced from a process for the manufacture of polyethylene terephthalate comprising the steps of:
    (a) providing ethylene glycol distillation bottoms from an ethylene glycol recovery unit associated with the manufacture of polyethylene terephthalate, the bottoms containing an alkali metal organic salt produced during the manufacture of polyethylene terephthalate, the alkali metal organic salt being in excess of about 100 ppm of the bottoms;
    (b) stripping the alkali metals from the organic acid by use of a strong acid; and
    (c) depolymerizing the organic acid.

2. The process according to claim 1 wherein the strong acid is selected from the group consisting of sulfuric acid, hydrochloric acid, nitric acid, phosphoric acid, or a combination thereof.

3. The process according to claim 1 wherein the depolymerization step further comprises:
    (i) glycolyzing the organic acid to bis-(2-hydroxyethyl) terephthalate; and
    (ii) methanolyzing the bis-(2-hydroxyethyl) terephthalate to dimethyl terephthalate.

4. The process according to claim 1 further comprising the step of adding water to the bottoms prior to stripping.

5. The process according to claim 4 further comprising the step of: stripping the mixture of alkali metal organic salt and water by adding a sufficient amount of a strong acid so that the mixture obtains a $pH \leq 2$.

6. The process according to claim 5 further comprising the step of: dewatering the product from the stripping step.

7. The process according to claim 6 wherein dewatering is accomplished by either filtration or centrifugation.

* * * * *